US00PP28965P2

(12) United States Plant Patent
Benetka

(10) Patent No.: US PP28,965 P2
(45) Date of Patent: Feb. 20, 2018

(54) ***WEIGELA* PLANT NAMED 'VUKOZ045203'**

(50) Latin Name: ***Weigela* hybrid**
Varietal Denomination: VUKOZ045203

(71) Applicant: Vojtech Benetka, Chodov (CZ)

(72) Inventor: Vojtech Benetka, Chodov (CZ)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/330,317

(22) Filed: Sep. 2, 2016

(51) Int. Cl.
*A01H 5/02* (2006.01)

(52) U.S. Cl.
USPC ..... Plt./226

(58) Field of Classification Search
USPC ..... Plt./226
See application file for complete search history.

*Primary Examiner* — Anne M Grunberg
(74) *Attorney, Agent, or Firm* — Cassandra Bright

(57) ABSTRACT

A new and distinct *Weigela* plant named 'VUKOZ045203' is disclosed, characterized by abundant flowering and reblooming of fuchsia-pink flowers. Plants have a a low growth habit. The new variety is a *Weigela*, normally produced as an outdoor garden plant.

2 Drawing Sheets

Latin name of the genus and species: *Weigela* hybrid.
Variety denomination: 'VUKOZ045203'.

BACKGROUND OF THE INVENTION

The new *Weigela* cultivar is a product of a planned breeding program conducted by the inventor, Vojtech Benetka, in Pruhonice, Czech Republic. The objective of the breeding program was to produce new *Weigela* varieties with low growth habit. The cross resulting in this new variety was made in 2004.

The seed parent is a proprietary, unpatented, *Weigela* referred to as '99-9-220'. The pollen parent is a proprietary, unpatented, *Weigela* referred to as '99-7-203'. The new variety was identified as a potentially interesting selection in 2008, at a research nursery in Pruhonice, Czech Republic.

Asexual reproduction of the new cultivar 'VUKOZ045203' by softwood cuttings was first performed in 2008, at a research nursery in Pruhonice, Czech Republic. Subsequent propagation has shown that the unique features of this cultivar are stable and reproduced true to type in five successive generations.

SUMMARY OF THE INVENTION

The cultivar 'VUKOZ045203' has not been observed under all possible environmental conditions. The phenotype may vary somewhat with variations in environment such as temperature, day length, and light intensity; without, however, any variance in genotype.

The following traits have been repeatedly observed and are determined to be the unique characteristics of 'VUKOZ045203' These characteristics in combination distinguish 'VUKOZ045203' as a new and distinct *Weigela* cultivar:

1. Low growth habit.
2. Fuchsia-pink flowers
3. Abundant flowering.
4. Re-blooming.

PARENT COMPARISON

Plants of the new cultivar 'VUKOZ045203' are similar to plants of the seed parent in most horticultural characteristics, however, plants of the new cultivar 'VUKOZ045203' differ in the following;

1. New cultivar has fuchsia-pink flowers, whereas the parent has dark crimson flowers.

Plants of the new cultivar 'VUKOZ045203' are similar to plants of the pollen parent in most horticultural characteristics, however, plants of the new cultivar 'VUKOZ045203' differ in the following;

1. New cultivar has fuchsia-pink flowers, whereas the parent has light crimson flowers.
2. New cultivar has a normal flower size, whereas the parent has an exceptionally small flower size.

COMMERCIAL COMPARISON

Plants of the new cultivar 'VUKOZ045203' can be compared to the unpatented commercial variety *Weigela* 'Verweig-6'. These varieties are similar in most horticultural characteristics; however 'VUKOZ045203' differs in the following:

1. New cultivar has fuchsia-pink flowers whereas this comparator has flowers that are mainly red.
2. New cultivar has a larger flower size than the comparator

BRIEF DESCRIPTION OF THE PHOTOGRAPHS

Figure 1:
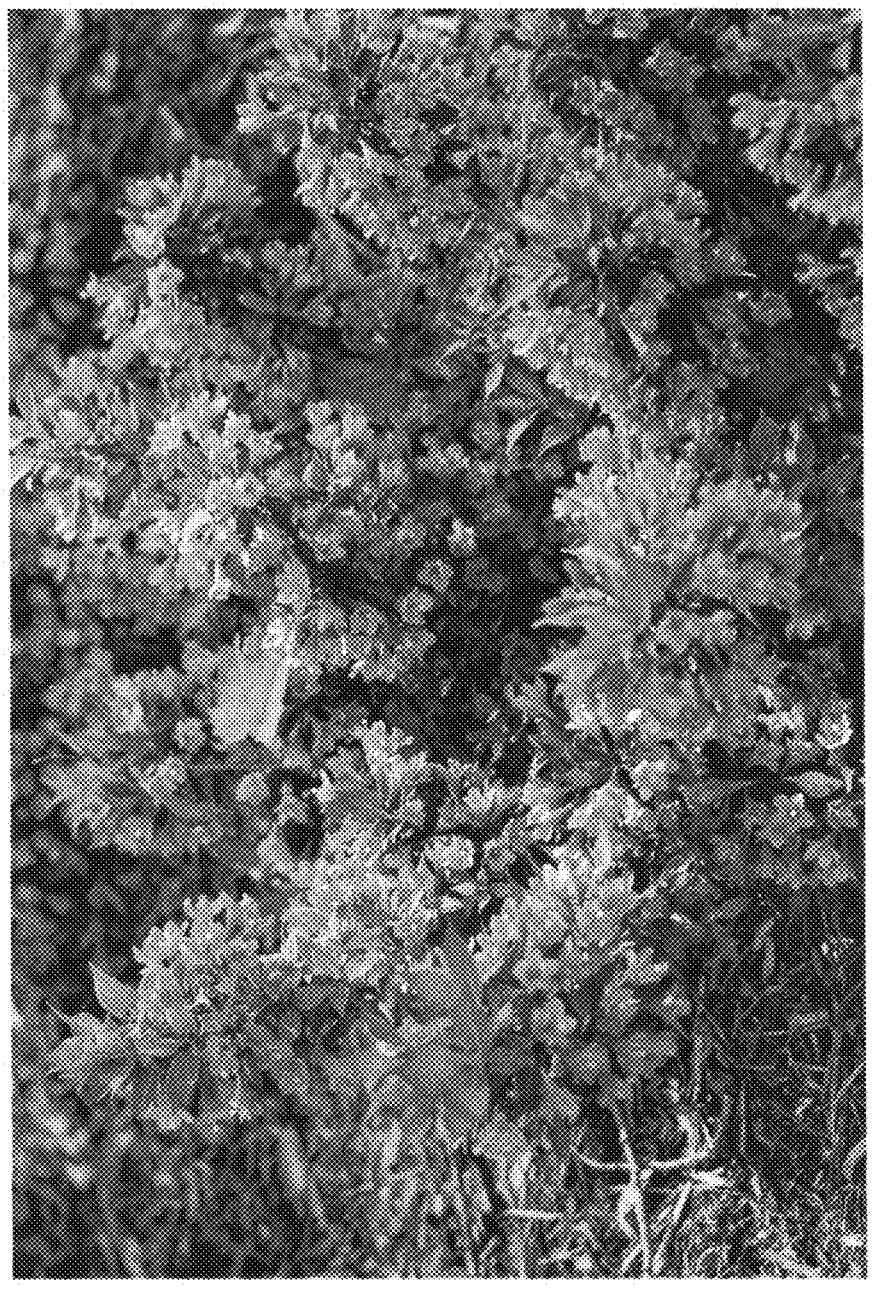

The accompanying photograph in FIG. 1 illustrates in full color a typical plant of 'VUKOZ045203' grown in an outdoor flower bed.

Figure 2:
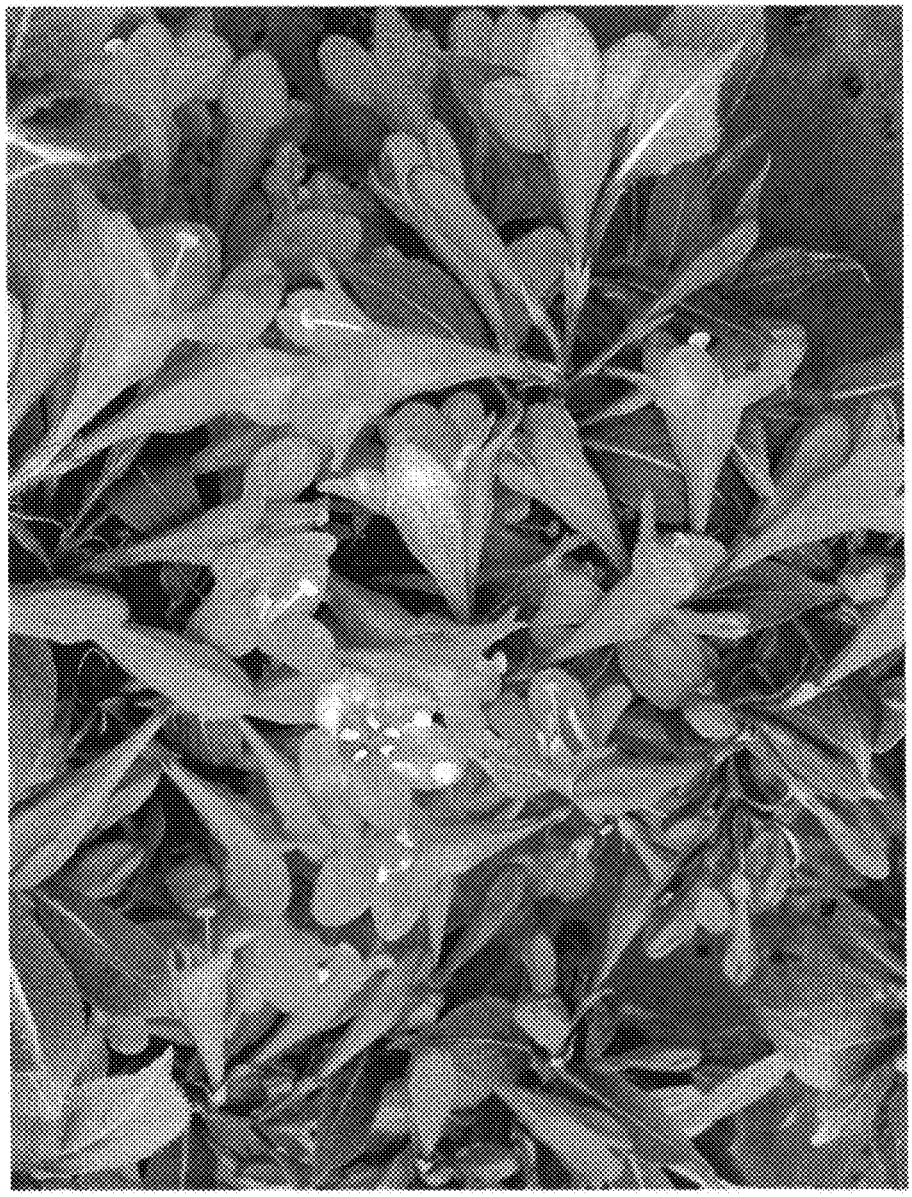

FIG. 2 illustrates a close-up view of flowers and foliage. Age of the plant photographed is approximately 2 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1996 except where general terms of ordinary dictionary significance are used. The following observations and measurements describe 'VUKOZ045203' plants grown in a polyhouse in Grand Haven, Mich. Measurements were taken during late Spring. The plants were 2 years old. The growing temperature ranged from approximately 5° C. to 27° C. Measurements and numerical values represent averages of typical plant types.

Botanical classification: *Weigela hybrida* 'VUKOZ045203'.

PROPAGATION

Time to initiate roots: Approximately 15 days.

Root description: Density is dense and freely branching. Thin root thickness. White in color, not effectively measured with a color chart.

Time to produce a rooted young plant: Approximately 60 days.

PLANT

Plant type: Shrub.

Age of plant described: Approximately 2 years old.

Growth habit: Compact growth with good branching.

Pot size of plant described: 2 gallon container.

Overall plant shape: Upright and Rounded.

Height: 53 cm.

Plant spread: 67 cm.

Growth rate: Medium.

Plant vigor: Strong.

Branching characteristics: Opposite.

Length of primary lateral branches: 57 cm.

Diameter of lateral branches: 8.5 mm.

Quantity of lateral branches: 18.

Stem:

- *Stem appearance*.—Round.
- *Stem strength*.—Strong.
- *Aspect*.—40° to 45°.
- *Color*.—Near RHS Yellow-Green 145C.
- *Pubescence*.—Yes.

Internode length: 1.7 cm.

FOLIAGE

Leaf:

- *Arrangement*.—Opposite.
- *Leaf shape*.—Ovate-oblanceolate.
- *Average length*.—Approximately 4.8 cm.
- *Average width*.—Approximately 2.0 cm.
- *Apex*.—Acuminate-Acute.
- *Base*.—Cuneate-Attenuate.
- *Margin*.—Serrulate.
- *Texture of top surface*.—Slight pubescence.
- *Texture of bottom surface*.—Pubescent, to a greater extent than upper surface.
- *Color*.—Young foliage upper side: Near RHS Green 143A. Young foliage under side: Near RHS Green 141C. Mature foliage upper side: Near RHS Green 143A. Mature foliage under side: Near RHS Green 141C.
- *Venation*.—Pattern: Pinnate. Color upper side: Near RHS Yellow-Green 153A. Color under side: Near RHS Yellow-Green 145A.
- *Petiole*.—Length: 4.0 mm. Diameter: 1.5 mm. Petiole color upper side: Near RHS Green 145A. Petiole color lower side: Near RHS Green 145B. Petiole Texture: Pubescent.
- *Foliage durability*.—Very durable.

FLOWER

Natural flowering season: Late spring to summer.

Inflorescence type and habit: Umbel to panicle.

Inflorescence height: 6.0 cm.

Inflorescence width: 6.2 cm.

Quantity of flowers per inflorescence: 4 to 8.

Quantity of flowers per plant: Hundreds.

Individual Flowers:

- *Flower shape*.—Salverform.
- *Flower aspect*.—Upward and slightly outward.
- *Flowering arrangement*.—Salverform flowers in groups of 2 to 4 most common.
- *Size*.—Diameter: Approximately 2.9 cm. Depth: Approximately 4.0 cm.
- *Flower other characteristics*.—Persistence: Self cleaning. Fragrance: Little to no floral scent.

Bud:

- *Shape*.—Obovate to spatulate.
- *Length*.—3.0 cm.
- *Diameter*.—7.5 mm.
- *Color*.—Near RHS Red-Purple 71A.

Petal:

- *Petal arrangement*.—Whorled, fused at opening of throat.
- *Number of petals per flower*.—5.
- *Petal shape*.—Obovate to oblanceolate.
- *Petal base*.—Fused at throat.
- *Margin*.—Entire, slightly undulate.
- *Tip shape*.—Obtuse.
- *Length*.—1.2 cm.
- *Width*.—1.0 cm.
- *Texture*.—Upper: Smooth. Lower: Smooth.
- *Petal color*.—When opening: Upper surface: Near RHS Red-Purple 70B with Red-Purple 70A along margin and few stripes of Red-Purple 64B. Lower surface: Near RHS Red-Purple 70B with Red-Purple 70A along margin. Fully opened: Upper surface: Near RHS Red-Purple 70B with Red-Purple 70A along margin and few stripes of Red-Purple 71B. Lower surface: Near RHS Red-Purple 70B with Red-Purple 70A along margin. Fades to: Near RHS Red-Purple 65B with Red-Purple 71C along margin.
- *Flower tube*.—Length: 3.0 cm. Diameter, base: 2.0 mm. Color: Near RHS Red-Purple 70C blended with Red-Purple Group 71C.
- *Throat*.—Texture: Smooth. Color: Near RHS Red-Purple 70C with a single spot of Red-Purple 63A blended with Orange 24B.

Sepal:

*Arrangement*.—Unguiculate, fused at base.
*Appearance*.—Long, narrowly triangular.
*Number*.—5.
*Shape*.—Narrowly triangular.
*Tip*.—Acute.
*Base*.—Obtuse.
*Margin*.—Entire.
*Length*.—5.0 mm.
*Width*.—1.5 mm.
*Texture, upper*.—Smooth, coriaceous.
*Texture, lower*.—Smooth, coriaceous.
*Color*.—Upper surface at maturity: Near RHS Red-Purple 63A blended with Yellow-Green 145A. Under surface at maturity: Near RHS Red-Purple 63A blended with Yellow-Green 145A.

Peduncle:

*Length*.—5.0 mm.
*Diameter*.—1.5 mm.
*Color*.—Near RHS Yellow-Green 144A.
*Orientation*.—Upright/outward.
*Strength*.—Good.
*Texture*.—Smooth, coriaceous, slightly pubescent.

Pedicel:

*Length*.—1.2 cm.
*Diameter*.—1.5 mm.
*Angle*.—Upright and outward.
*Strength*.—Good.
*Texture*.—Smooth, coriaceous, slightly pubescent.
*Color*.—Near RHS Red-Purple 63A blended with Yellow-Green 145A.

REPRODUCTIVE ORGANS

Stamens:

*Number*.—5.
*Filament length*.—2.3 cm.
*Filament color*.—Near RHS White 155B fading to Red-Purple 63B.

Anthers:

*Shape*.—Linear, slightly oblong.
*Length*.—4.0 mm.
*Color*.—Near RHS White 155B.
*Pollen color*.—Near RHS White 155B.
*Pollen amount*.—Some.

Pistil:

*Number*.—1 per flower.
*Length*.—3.1 cm.
*Style*.—Length: 3.0 cm. Color: Near RHS White 155B.
*Stigma*.—Color: Near RHS White 155B. Shape: Globular, flat-bottomed.

OTHER CHARACTERISTICS

Seeds and fruits: Not observed.

Disease/pest resistance: Neither resistance nor susceptibility to normal diseases and pests of *Weigela* have been observed.

Temperature tolerance: The new variety has been observed to tolerate temperatures between −31° C. to 38° C.

Environmental stressors: Good resistance to wind and rain.

What is claimed is:

1. A new and distinct cultivar of *Weigela hybrida* plant named 'VUKOZ045203' as herein illustrated and described.

* * * * *